(12) United States Patent
Tsuchiya et al.

(10) Patent No.: US 11,013,517 B2
(45) Date of Patent: May 25, 2021

(54) CLIP TREATMENT TOOL

(71) Applicant: FUJIFILM Corporation, Tokyo (JP)

(72) Inventors: Syuji Tsuchiya, Kanagawa (JP); Koji Itoh, Kanagawa (JP); Issei Suzuki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/714,800

(22) Filed: Dec. 16, 2019

(65) Prior Publication Data

US 2020/0113568 A1 Apr. 16, 2020

Related U.S. Application Data

(63) Continuation of application No. PCT/JP2018/015206, filed on Apr. 11, 2018.

(30) Foreign Application Priority Data

Jun. 21, 2017 (JP) .............................. JP2017-121591

(51) Int. Cl.
*A61B 17/122* (2006.01)
*A61B 17/08* (2006.01)
(Continued)

(52) U.S. Cl.
CPC .......... *A61B 17/122* (2013.01); *A61B 17/083* (2013.01); *A61B 17/10* (2013.01);
(Continued)

(58) Field of Classification Search
CPC ..... A61B 17/083; A61B 17/10; A61B 17/122; A61B 17/128; A61B 17/1285; A61B 2017/12004
See application file for complete search history.

(56) References Cited

U.S. PATENT DOCUMENTS

| 5,520,701 A | 5/1996 | Lerch |
| 7,452,327 B2 | 11/2008 | Durgin et al. |

(Continued)

FOREIGN PATENT DOCUMENTS

| EP | 1604614 | 12/2005 |
| JP | 2008289524 | 12/2008 |

(Continued)

OTHER PUBLICATIONS

Office Action of Japan Counterpart Application, with English translation thereof, dated Nov. 4, 2020, pp. 1-10.
(Continued)

*Primary Examiner* — Melanie R Tyson
(74) *Attorney, Agent, or Firm* — JCIPRNET

(57) ABSTRACT

A clip treatment tool includes: a clip body that has two arm portions and a folded portion, the two arm portions, the folded portion connecting proximal end parts of the two arm portions; a tightening ring that functions to close the two arm portions in accordance with movement of the clip body from a distal end side toward a proximal end side; a pressing tube that has at least one opening formed in an outer surface thereof, and that allows the clip body to be contained therein in accordance with the movement of the clip body; and a coupling member that has a distal end part to which the folded portion is removably connected and a proximal end part to which a distal end part of an operation wire is fixed, the coupling member coupling the clip body and the operation wire to each other.

9 Claims, 11 Drawing Sheets

(51) Int. Cl.
*A61B 17/128* (2006.01)
*A61B 17/10* (2006.01)
*A61B 17/12* (2006.01)

(52) U.S. Cl.
CPC ........ *A61B 17/128* (2013.01); *A61B 17/1285* (2013.01); *A61B 2017/12004* (2013.01)

(56) References Cited

U.S. PATENT DOCUMENTS

| | | | |
|---|---|---|---|
| 8,083,668 | B2 | 12/2011 | Durgin et al. |
| 8,974,371 | B2 | 3/2015 | Durgin et al. |
| 9,339,270 | B2 | 5/2016 | Martinez et al. |
| 9,370,371 | B2 | 6/2016 | Durgin et al. |
| 9,949,740 | B2 | 4/2018 | Satake et al. |
| 9,980,725 | B2 | 5/2018 | Durgin et al. |
| 2011/0054498 | A1* | 3/2011 | Monassevitch .... A61B 17/1285 606/142 |
| 2014/0171973 | A1 | 6/2014 | Zhu |
| 2016/0367258 | A1 | 12/2016 | Jin et al. |
| 2018/0193022 | A1 | 7/2018 | Satake et al. |
| 2018/0235608 | A1 | 8/2018 | Durgin et al. |

FOREIGN PATENT DOCUMENTS

| | | |
|---|---|---|
| JP | 2009189705 | 8/2009 |
| JP | 4921173 | 4/2012 |
| JP | 5750619 | 7/2015 |

OTHER PUBLICATIONS

"International Search Report (Form PCT/ISA/210) of PCT/JP2018/015206," dated Jun. 26, 2018, with English translation thereof, pp. 1-3.

"Written Opinion of the International Searching Authority (Form PCT/ISA/237) of PCT/ JP2018/015206," dated Jun. 26, 2018, with English translation thereof, pp. 1-12.

"Search Report of Europe Counterpart Application", dated Apr. 23, 2020, p. 1-p. 7.

* cited by examiner

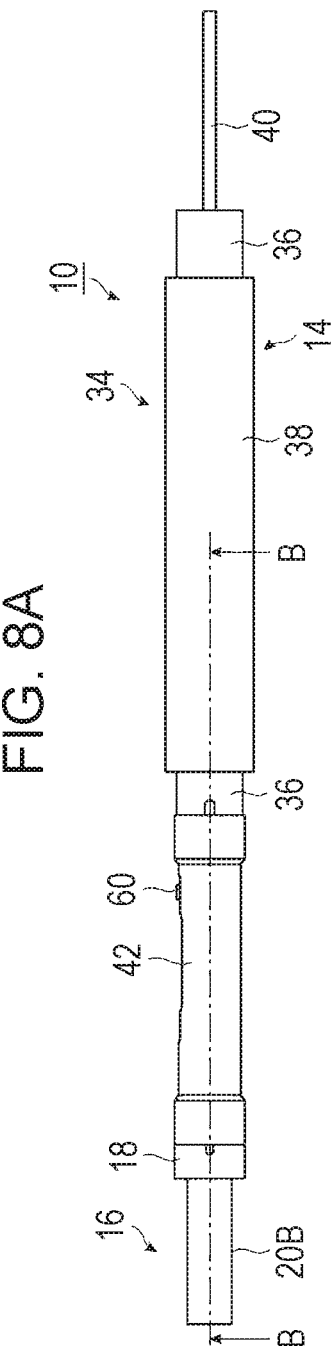
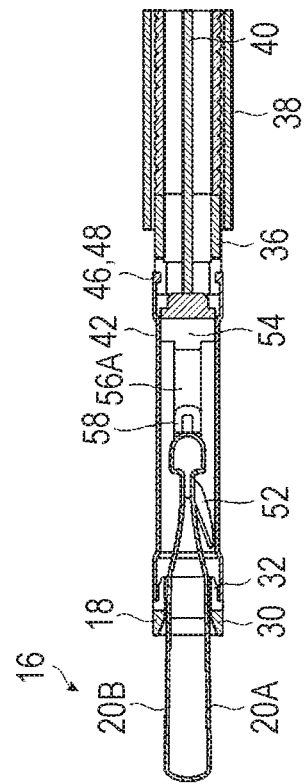
FIG. 8A
FIG. 8B

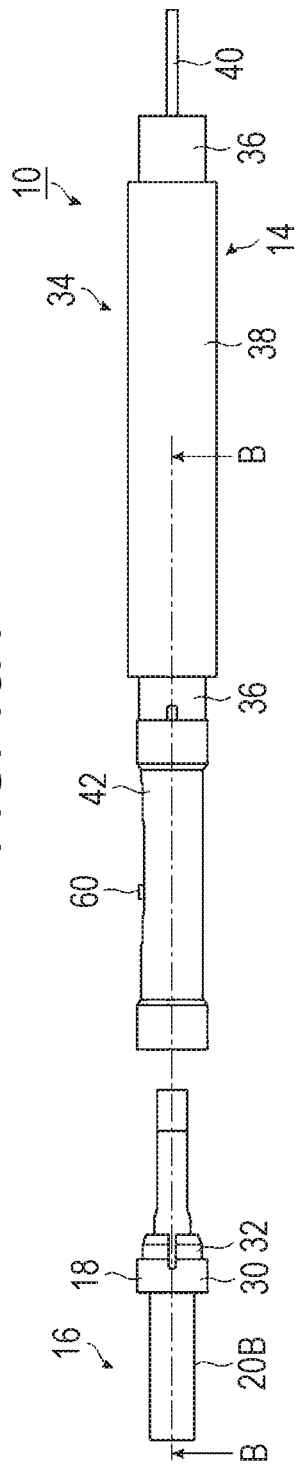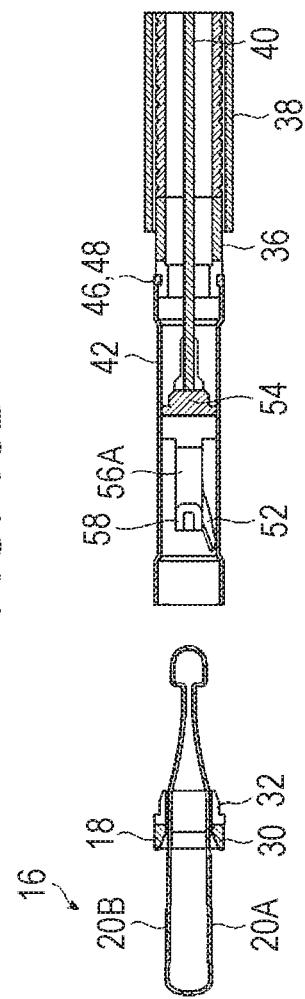

CLIP TREATMENT TOOL

CROSS-REFERENCE TO RELATED APPLICATIONS

This application is a Continuation of PCT International Application No. PCT/JP2018/015206 filed on Apr. 11, 2018, which claims priority under 35 U.S.C § 119(a) to Japanese Patent Application No. 2017-121591 filed on Jun. 21, 2017. Each of the above application(s) is hereby expressly incorporated by reference, in its entirety, into the present application.

BACKGROUND OF THE INVENTION

1. Field of the Invention

The present invention relates to a clip treatment tool for an endoscope, which is used, for example, to close a wound and to stop bleeding in a living body.

2. Description of the Related Art

A clip treatment tool for an endoscope is used, for example, to close a wound and to stop bleeding by extruding arm portions of a clip from a distal end of the endoscope, which is inserted into a living body, and by ligating a treatment part, such as the wound and the bleeding part, with distal end parts of the arm portions of the clip.

Examples of such a clip treatment tool known to date include clip treatment tools that can freely open and close arm portions of a clip (see JP5750619B, JP4921173B, U.S. Pat. No. 9,339,270B, US2016/0367258A, and JP2008-289524A). By using these known technologies, for example, it is possible to freely open and close arm portions of a clip in the body of a patient to hold a treatment part over again, and therefore it is possible to apply the clip to an accurate position on the treatment part and to perform treatment such as stoppage of bleeding.

SUMMARY OF THE INVENTION

However, once the treatment part has been ligated by the clip, the clip is placed in the body of the patient. Therefore, when the clip is placed in the body at a position displaced from a target position to be ligated due to an erroneous operation or the like, and when, for example, the clip placed in the body becomes unnecessary after the objective of using the clip, such as stoppage of bleeding, has been sufficiently achieved, the clip remains placed in the living body, and it is necessary to wait until the clip is naturally removed due to a change in body tissue of the patient. That is, there is a problem in that it is not possible to remove the clip at a desirable timing.

An object of the present invention is to provide a clip treatment tool with which, after the clip has been once applied, it is possible to reliably maintain the applied state, and it is possible to remove a clip placed in a living body at any desirable timing.

In order to achieve the object, the present invention provides a clip treatment tool including: a clip body that has two arm portions that face each other and open and close and a folded portion that connects proximal end parts of the two arm portions; a tightening ring that is attached to the two arm portions of the clip body and that functions to close the two arm portions in accordance with movement of the clip body from a distal end side toward a proximal end side; a pressing tube that has at least one opening formed in an outer surface thereof and extending in an axial direction, that has a distal end part to which the tightening ring is removably attached, and that allows the clip body to be contained therein in accordance with movement of the clip body from the distal end side toward the proximal end side; and a coupling member that has a distal end part to which the folded portion is removably connected and a proximal end part to which a distal end part of an operation wire is fixed, the coupling member coupling the clip body and the operation wire to each other. The coupling member is contained in the pressing tube.

Preferably, the coupling member has an exposed portion at least a part of which is exposed from the opening, the exposed portion moves in the opening in the axial direction from the proximal end side toward the distal end side in accordance with movement of the coupling member from the proximal end side toward the distal end side, and the exposed portion moves in the opening in the axial direction from the distal end side toward the proximal end side in accordance with movement of the coupling member from the distal end side toward the proximal end side.

Preferably, the opening has a first opening region, a second opening region, and a third opening region in order from the distal end side; and the two arm portions open in accordance with movement of the exposed portion in the first opening region from the proximal end side toward the distal end side, and the two arm portions close in accordance with movement of the exposed portion in the first opening region from the distal end side toward the proximal end side.

Preferably, in accordance with movement of the exposed portion in the first opening region from the distal end side toward the proximal end side, the two arm portions are pressed by an end part of the tightening ring on the distal end side in directions toward each other and elastically deform, and the two arm portions gradually close from an open state and enter a closed state; and, in accordance with movement of the exposed portion in the first opening region from the proximal end side toward the distal end side, the two arm portions gradually open from the closed state due to an elastic force and enter the open state.

Preferably, when the exposed portion moves to a boundary between the first opening region and the second opening region, the tightening ring and the two arm portions are latched to each other and the two arm portions enter the closed state, and the clip body is locked to the tightening ring while the two arm portions are in the closed state.

Preferably, the coupling member has a clamping portion, the clamping portion has a first clamping member and a second clamping member, and the first clamping member has a latch portion on an inner surface of the first claiming member on the distal end side, the inner surface facing the second clamping member; the folded portion is clamped by the first clamping member and the second clamping member, the folded portion and the latch portion are latched to each other, and the coupling member and the clip body are latched to each other; and in a state in which the clip body is locked to the tightening ring, in accordance with movement of the exposed portion in the second opening region from the distal end side toward the proximal end side, the latch portion moves onto an end part of the folded portion on the proximal end side and moves from the distal end side toward the proximal end side, a distal end part of the first clamping member moves from the opening toward an outside of the pressing tube, the exposed portion moves from the second opening region into the third opening region, the latch portion moves over the end part of the folded portion on the proximal end side, the folded portion and the latch portion are unlatched from each other, and the clip body and the coupling member are separated from each other.

Preferably, in a state in which the clip body and the coupling member are separated from each other, in accordance with movement of the operation wire from the proximal end side toward the distal end side, the coupling member moves from the proximal end side toward the distal end side, a proximal end part of the clip body is pushed toward the distal end side by the coupling member, and the tightening ring to which the clip body is locked and the pressing tube are separated from each other.

Preferably, each of the two arm portions has, at both end parts thereof in a width direction, a recessed portion having a length in an extension direction larger than a size of the tightening ring in the axial direction; when the clip body moves from the distal end side toward the proximal end side and end parts of the recessed portions on the proximal end side move to positions beyond an end part of the tightening ring on the proximal end side, the two arm portions move in directions away from each other due to an elastic force, the tightening ring is latched to the recessed portions, and the clip body is locked to the tightening ring; in a state in which the tightening ring and the pressing tube are separated from each other, the tightening ring is squeezed from both sides of an outer peripheral surface thereof in directions in which the two arm portions face each other, the end parts of the recessed portions on the proximal end side move to positions where the end parts contact an inner peripheral surface of the tightening ring, and the clip body and the tightening ring are unlocked; and, in a state in which the clip body and the tightening ring are unlocked, in accordance with movement of the tightening ring relative to the clip body from the distal end side toward the proximal end side, the two arm portions open from the closed state and enter the open state.

Preferably, each of the two arm portions has, at both end parts thereof in a width direction, a recessed portion having a length in an extension direction larger than a size of the tightening ring in the axial direction; when the clip body moves from the distal end side toward the proximal end side and end parts of the recessed portions on the proximal end side move to positions beyond an end part of the tightening ring on the proximal end side, the two arm portions move in directions away from each other due to an elastic force, the tightening ring is latched to the recessed portions, and the clip body is locked to the tightening ring; in a state in which the tightening ring and the pressing tube are separated from each other, the two arm portions are pressed from both sides of outer surfaces thereof in directions in which the two arm portions face each other, the end parts of the recessed portions on the proximal end side move to positions where the end parts contact an inner peripheral surface of the tightening ring, and the clip body and the tightening ring are unlocked; and, in a state in which the clip body and the tightening ring are unlocked, in accordance with movement of the clip body relative to the tightening ring from the proximal end side toward the distal end side, the two arm portions open from the closed state and enter the open state.

With the present invention, until a treatment part is ligated by a clip unit, which is composed of the clip body and the tightening ring, it is possible to hold the treatment part over again by using the two arm portions; and, after the treatment part has been ligated by the clip unit, because the clip body and the tightening ring are locked, it is possible to reliably maintain the state in which the treatment part is ligated by the clip unit. Moreover, after the clip unit is placed at the treatment part, it is possible to remove the clip unit from the treatment part by unlocking the clip body and the tightening ring at any desirable timing.

BRIEF DESCRIPTION OF THE DRAWINGS

FIG. 8A is a partial external side view of the clip treatment tool according to the embodiment illustrated in FIG. 7A, as seen in a different direction;

FIG. 8B is a sectional view taken along a chain line B-B in FIG. 8A;

FIG. 10A is a partial external side view of the clip treatment tool according to the embodiment illustrated in FIG. 9A, as seen in a different direction;

FIG. 10B is a sectional view taken along a chain line B-B in FIG. 10A;

DESCRIPTION OF THE PREFERRED EMBODIMENTS

Figure 1A:
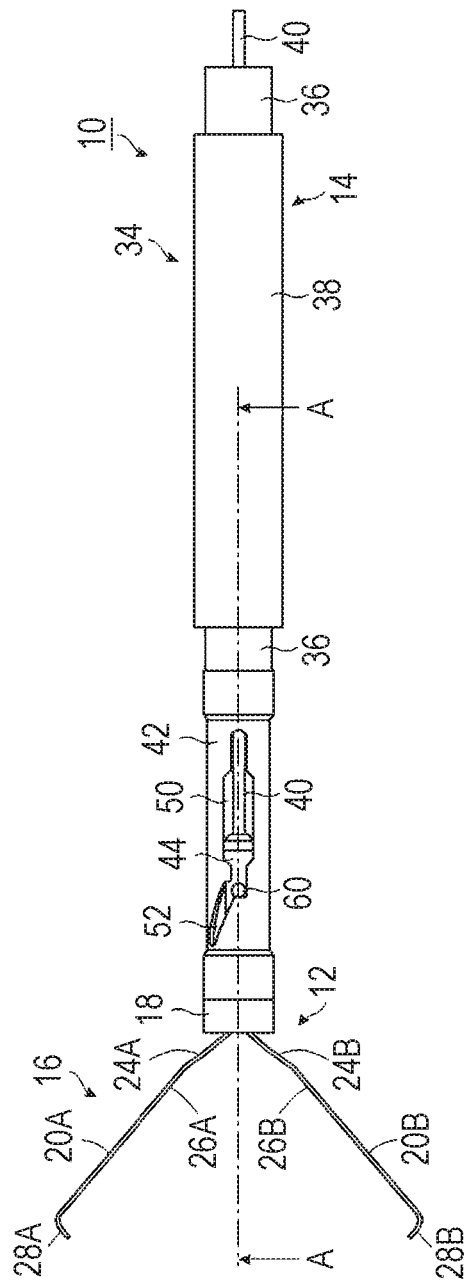
FIG. 1A is a partial external side view of a clip treatment tool according to an embodiment of the present invention, in a state in which two arm portions of a clip body are in an open state.

Hereafter, a clip treatment tool according to the present invention will be described in detail based on preferred embodiments illustrated in the drawings.

Figure 1B:
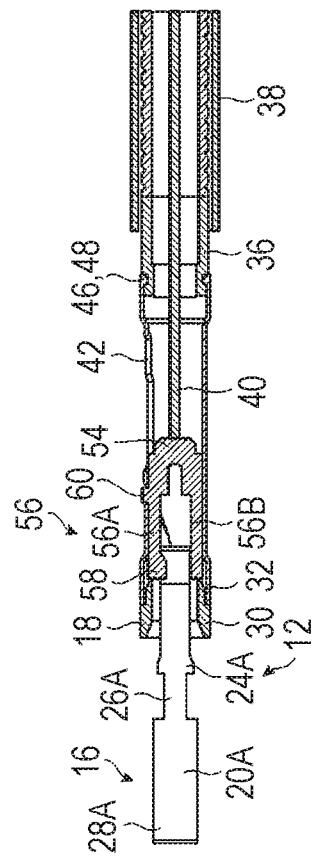
FIG. 1B is a sectional view taken along a chain line A-A in FIG. 1A.
Figure 2A:
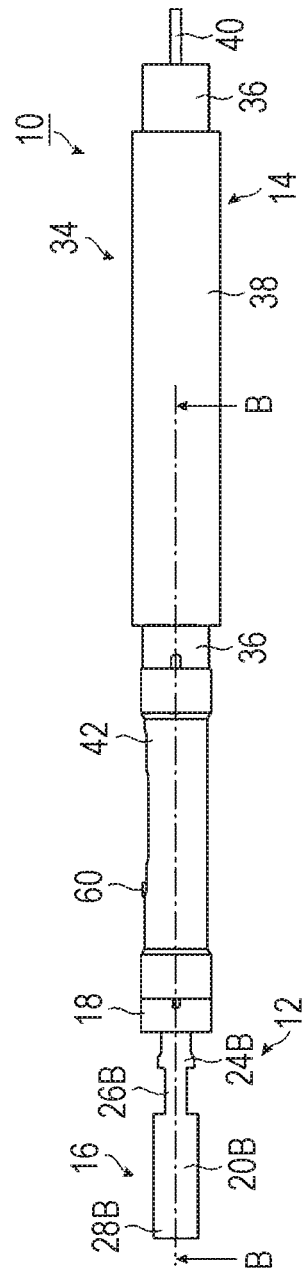
FIG. 2A is a partial external side view of the clip treatment tool according to the embodiment illustrated in FIG. 1A, as seen in a different direction.
Figure 2B:
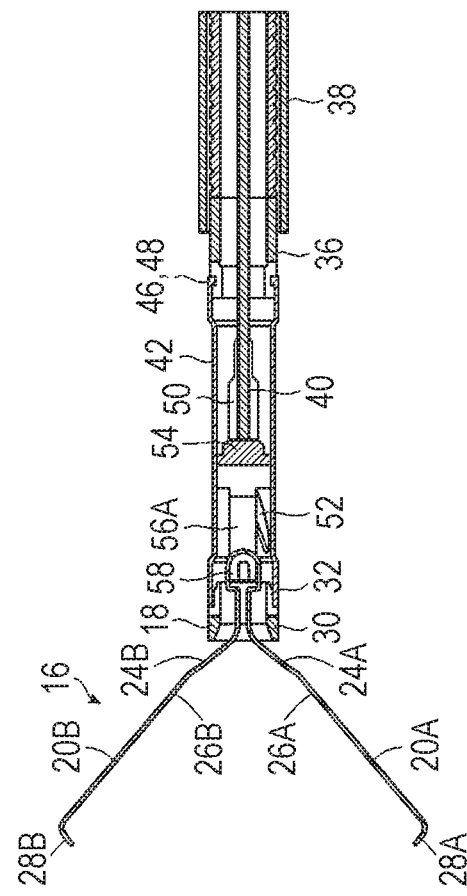
FIG. 2B is a sectional view taken along a chain line B-B in FIG. 2A.

FIG. 1A is a partial external side view of a clip treatment tool according to an embodiment of the present invention, in a state in which two arm portions of a clip body are in an open state. FIG. 1B is a sectional view taken along a chain line A-A in FIG. 1A. FIG. 2A is a partial external side view of the clip treatment tool according to the embodiment illustrated in FIG. 1A, as seen in a different direction. FIG. 2B is a sectional view taken along a chain line B-B in FIG. 2A.

In the present embodiment, a first direction is defined as the direction in which the two arm portions of the clip body face each other (direction perpendicular to the plane of FIG. 1B), and a second direction is defined as the direction perpendicular to both of the first direction and the axial direction of a pressing tube (direction perpendicular to the plane of FIG. 1A). In the clip treatment tool, a side on which a treatment part is located is defined as the distal end side, and a side on which an operator is located is defined as the proximal end side.

In all figures, in order to facilitate understanding, the dimensions, such as the thickness and the length, of each element of the present embodiment are appropriately changed from the actual dimensions, as necessary.

A clip treatment tool 10 illustrated in FIGS. 1A, 1B, 2A, and 2B includes a clip unit 12 and a treatment tool body 14. When operated by an operator, for example, the clip treatment tool 10 is inserted from a treatment tool inlet of an operation portion of an endoscope, is extruded from a treatment tool outlet of a distal end surface of an insertion portion of the endoscope that has been inserted into the body of a patient, and ligates a treatment part by using the clip unit 12.

The clip unit 12 includes a clip body 16 and a tightening ring 18.

Figure 3:
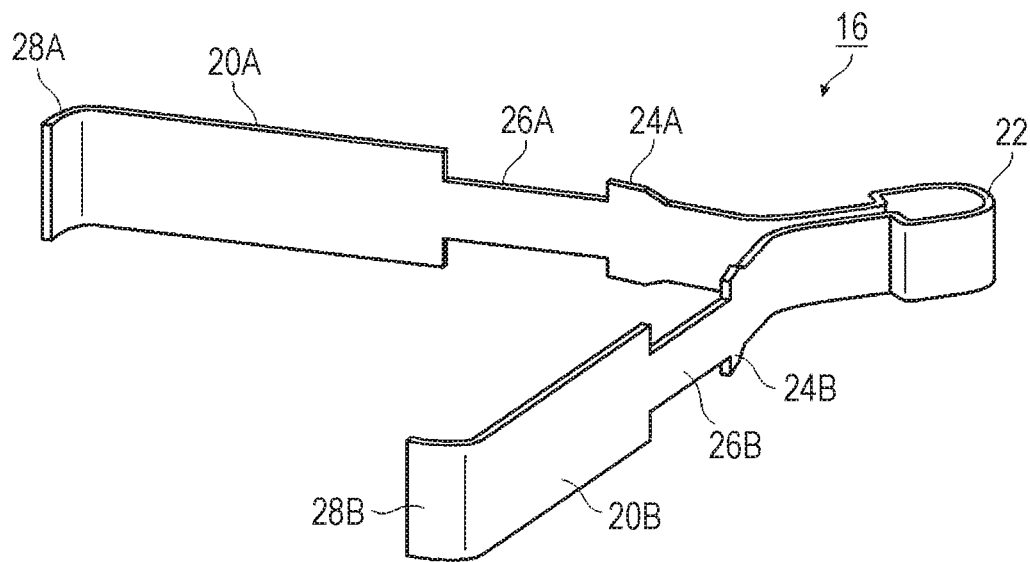
FIG. 3 is an external perspective view of the clip body according to the embodiment.

FIG. 3 is an external perspective view of the clip body according to the embodiment.

As illustrated in FIG. 3, the clip body 16 has two arm portions, which are a first arm portion 20A and a second arm portion 20B, that face each other and that open and close, and a folded portion 22 that connects proximal end parts of the two arm portions 20A and 20B.

The two arm portions 20A and 20B and the folded portion 22 are integrally formed by being bent respectively at a position between the first arm portion 20A and the folded portion 22 and a position between the second arm portion 20B and the folded portion 22. The folded portion 22 has a substantial C-shape, as seen in the second direction. The two arm portions 20A and 20B face each other, and, in a state in which an external force is not applied, extend so as to become farther from each other from the proximal end side toward the distal end side.

The first arm portion 20A has a first protruding portion 24A, a first recessed portion 26A, and a first claw portion 28A, in order from the proximal end side.

The first protruding portion 24A is formed between a proximal end part of the first arm portion 20A and the first recessed portion 26A. The first protruding portion 24A has, at both end parts of the first arm portion 20A in the width direction (the second direction), an inclined part whose size in the width direction increases from the proximal end side toward the distal end side, and a flat part that is disposed on the distal end side of the inclined part and whose size in the width direction is constant.

The first recessed portion 26A is formed between the first protruding portion 24A and the first claw portion 28A. The first recessed portion 26A is formed, at both end parts of the first arm portion 20A in the width direction, so that the size thereof in the width direction is smaller than the size of each of the flat part of the first protruding portion 24A and the first claw portion 28A in the width direction. The first recessed portion 26A is formed so that the length thereof in the extension direction is slightly larger than the size of the tightening ring 18 in the axial direction.

The first claw portion 28A is formed at a distal end part of the first arm portion 20A. The first claw portion 28A is formed by bending the distal end part of the first arm portion 20A by a constant angle in a direction toward the second arm portion 20B.

The second arm portion 20B is configured similarly to the first arm portion 20A. The second arm portion 20B has a second protruding portion 24B, a second recessed portion 26B, and a second claw portion 28B, which are respectively formed at positons corresponding to the first protruding portion 24A, the first recessed portion 26A, and the first claw portion 28A of the first arm portion 20A.

The first protruding portion 24A and the second protruding portion 24B are portions that guide the tightening ring 18 to the first recessed portion 26A and the second recessed portion 26B. The first recessed portion 26A and the second recessed portion 26B are portions to which the tightening ring 18 is fitted. The first claw portion 28A and the second claw portion 28B are portions for holding a treatment part therebetween and ligating the treatment part.

As illustrated in FIGS. 1B and 2B, the tightening ring 18 has a tightening ring body 30 and an attachment portion 32 for attaching the tightening ring 18 to a pressing tube 42. The tightening ring body 30 and the attachment portion 32 are integrally formed.

The tightening ring body 30 is a portion that protrudes from a distal end part of the pressing tube 42 toward the distal end side when the tightening ring 18 is attached to the pressing tube 42. The outside diameter of the tightening ring body 30 is substantially the same as the outside diameter of the distal end part of the pressing tube 42. An inclined part, whose inside diameter gradually decreases from the distal end side toward the proximal end side, is formed along the entire periphery of the inner peripheral surface of a distal end part of the tightening ring body 30.

The attachment portion 32 is a portion that extends from a proximal end part of the tightening ring body 30 toward the proximal end side and that is inserted into the pressing tube 42 from the distal end part of the pressing tube 42. The outside diameter of the attachment portion 32 is slightly smaller than the inside diameter of the distal end part of the pressing tube 42.

As illustrated in FIGS. 1B and 2B, the tightening ring 18 is attached to the two arm portions 20A and 20B of the clip body 16 in a state before the clip body 16 is locked to the tightening ring 18, that is, in a state in which the two arm portions 20A and 20B are in an open state. To be more specific, the tightening ring 18 is attached to parts of the first arm portion 20A and the second arm portion 20B on the proximal end side relative to the first protruding portion 24A and the second protruding portion 24B.

The tightening ring 18 functions to open the two arm portions 20A and 20B in accordance with movement of the clip body 16 relative to the tightening ring 18 from the proximal end side toward the distal end side, and to close the two arm portions 20A and 20B in accordance with movement of the clip body 16 relative to the tightening ring 18 from the distal end side toward the proximal end side.

The clip body 16 and the tightening ring 18 of the clip unit 12 are made of a material such as a stainless steel, titanium, or a cobalt-chrome alloy. Accordingly, even after the clip unit 12 is placed in the body of a patient, the patient can have a magnetic resonance imaging (MRI) scan.

The treatment tool body 14 includes an insertion portion 34 and an operation portion (not shown).

The insertion portion 34 includes a coil sheath 36, a tube sheath 38, an operation wire 40, the pressing tube 42, and a coupling member 44.

The coil sheath 36 and the tube sheath 38 are flexible tubes that are made of, for example, a fluorocarbon resin such as polytetrafluoroethylene (PTFE) or a resin material such as high-density polyethylene (HDPE). The coil sheath 36 is inserted through the inside of the tube sheath 38. As illustrated in FIGS. 1B and 2B, a recessed portion 46 is formed along the entire periphery of an outer peripheral surface of a distal end part of the coil sheath 36.

The operation wire 40 is made from, for example, a single wire or a stranded wire made of a metal. The operation wire 40 is inserted through the inside of the coil sheath 36 so as to be movable in the axial direction of the coil sheath 36.

When an operator operates an operation portion of the clip treatment tool 10, the operation wire 40 moves in the coil sheath 36 toward the distal end side or the proximal end side. That is, the operator can push the operation wire 40 from the proximal end side toward the distal end side or pull the operation wire 40 from the distal end side toward the proximal end side.

The pressing tube 42 is made of, for example, a material such as a stainless steel, titanium, or a cobalt-chrome alloy.

The inside diameter and the outside diameter of a proximal end part and a distal end part of the pressing tube 42 are larger than the inside diameter of and the outside diameter of a middle part of the pressing tube 42 in the axial direction. As illustrated in FIGS. 1B and 2B, a protruding portion 48, which corresponds to the recessed portion 46 of the coil sheath 36, is formed along the entire periphery of an inner peripheral surface of the pressing tube 42 on the proximal end side. The inside diameter of the proximal end part of the pressing tube 42 is slightly larger than the outside diameter of the distal end part of the coil sheath 36. The proximal end part of the pressing tube 42 is attached to the distal end part of the coil sheath 36 by pressing the distal end part of the coil sheath 36 into the proximal end part of the pressing tube 42 and by fitting the protruding portion 48 of the pressing tube 42 and the recessed portion 46 of the coil sheath 36 to each other. The tightening ring 18 is removably attached to the distal end part of the pressing tube 42 by inserting the attachment portion 32 of the tightening ring 18 into the pressing tube 42 from the distal end part.

The pressing tube 42 allows the clip body 16 to be contained therein in accordance with movement of the clip body 16 relative to the pressing tube 42 from the distal end side toward the proximal end side.

Figure 4:
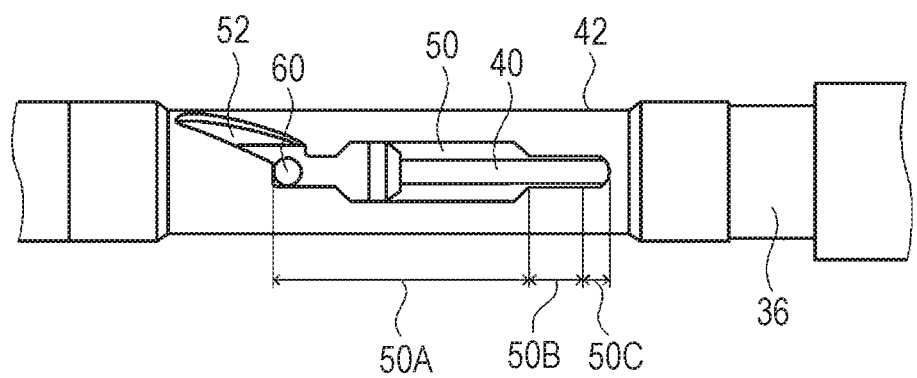
FIG. 4 is an enlarged external view of an opening of a pressing tube illustrated in FIG. 1A.

FIG. 4 is an enlarged external view of an opening of a pressing tube illustrated in FIG. 1A.

As illustrated in FIG. 4, in the outer surface of the pressing tube 42, at least one opening 50 extending in the axial direction of the pressing tube 42 is formed. The opening 50 extends, in a middle part of the pressing tube 42 in the axial direction, linearly from the proximal end side toward the distal end side. The opening 50 has a first opening region 50A, a second opening region 50B, and a third opening region 50C, in order from the distal end side.

The first opening region 50A includes a middle part in the extension direction of the opening 50 and an opening region on the distal end side relative to the middle part. The size of the middle part of the first opening region 50A in the width direction is larger than the size of a part of the first opening region 50A on the distal end side relative to the middle part.

The second opening region 50B is an opening region formed on the proximal end side of the first opening region 50A, that is, between the first opening region 50A and the third opening region. The third opening region 50C is an opening region formed on the proximal end side relative to the second opening region 50B. The size of each of the second opening region 50B and the third opening region 50C in the width direction is substantially the same as the size of the part of the first opening region 50A on the distal end side relative to the middle part.

As illustrated in FIG. 4, in a middle part of the outer surface of the pressing tube 42 in the axial direction, an opening 52, which extends further from a distal end part of the first opening region toward the distal end side so as to be inclined at a constant angle with respect to the axial direction, is formed.

The coupling member 44 has a coupling member body 54 and a clamping portion 56 as illustrated in FIG. 1B, and is made of, for example, a biocompatible resin. The coupling member 44 is contained in the pressing tube 42. A distal end part of the operation wire 40 is fixed to a proximal end part of the coupling member body 54, that is, a proximal end part of the coupling member 44.

The clamping portion 56 is a portion that serves as a distal end part to which the folded portion 22 of the clip body 16 is removably connected. The clamping portion 56 is disposed on the distal end side of the coupling member body 54, and the clamping portion 56 and the coupling member body 54 are integrally formed. The clamping portion 56 has a first clamping member 56A and a second clamping member 56B. The first clamping member 56A and the second clamping member 56B extend parallelly from a distal end part of the coupling member body 54 toward the distal end side so as to face each other. The first clamping member 56A and the second clamping member 56B are disposed with a constant distance therebetween in the second direction. The distance between the first clamping member 56A and the second clamping member 56B is slightly larger than the size of the folded portion 22 of the clip body 16 in the width direction.

The length of the first clamping member 56A in the extension direction is slightly smaller than the length of the middle part of the opening 50 of the pressing tube 42 in the axial direction. The size of the first clamping member 56A in the width direction (the first direction) is slightly smaller than the size of the middle part (the first opening region 50A) of the opening 50 of the pressing tube 42 in the width direction (the first direction). The outer surface of the first clamping member 56A faces in the direction toward the opening 50 of the pressing tube 42.

As illustrated in FIGS. 1B and 2B, the first clamping member 56A has a latch portion 58, which is latched to the folded portion 22 of the clip body 16, on an inner surface of a distal end portion thereof facing the second clamping member 56B. The latch portion 58 protrudes from the first clamping member 56A toward the second clamping member 56B. The latch portion 58 has an inclined part that is formed so that the height thereof in the second direction increases from the proximal end side toward the distal end side, and a flat part that is disposed on the distal end side of the inclined part and that has a constant height. The shape of the latch portion 58 as seen in the second direction is a substantial C-shape, which is the same as the shape of the folded portion 22 of the clip body 16 as seen in the second direction. The outside diameter of the shape of the latch portion 58 is slightly larger than the inside diameter of the shape of a space that is formed by the folded portion 22 when the folded portion 22 is seen in the second direction.

The folded portion 22 of the clip body 16 is clamped by the first clamping member 56A and the second clamping member 56B from both sides in the second direction; the latch portion 58, which protrudes from the first clamping member 56A toward the second clamping member 56B, is inserted into the space formed by the folded portion 22 when the folded portion 22 is seen in the second direction; the folded portion 22 and the latch portion 58 are latched to each other; and the coupling member 44 are the clip body 16 are removably latched to each other.

Because the distal end part of the coupling member 44 is removably latched to the folded portion 22 in this way and the distal end part of the operation wire 40 is fixed to the proximal end part of the coupling member 44, the clip body 16 and the operation wire 40 are coupled to each other by the coupling member 44.

In accordance with movement of the operation wire 40 from the proximal end side toward the distal end side, the coupling member 44 is moved in the pressing tube 42 from the proximal end side toward the distal end side. In accordance with movement of the operation wire 40 from the distal end side toward the proximal end side, the coupling member 44 is moved in the pressing tube 42 from the distal end side toward the proximal end side.

The coupling member 44 has an exposed portion 60, at least a part of which is exposed from the opening 50 of the pressing tube 42, on an outer surface thereof between the first clamping member 56A and the coupling member body 54. The size of the exposed portion 60 of the coupling member 44 in the width direction (the first direction) is slightly smaller than the size, in the width direction, of each of a part of the opening 50 of the pressing tube 42 on the distal end side relative to the middle part of the opening 50 (the first opening region), the second opening region 50B, the third opening region 50C, and the opening 52.

When inserting the coupling member 44 into the pressing tube 42 from the distal end part of the pressing tube 42, the opening 52 in the outer surface of the pressing tube 42 serves as a guide groove that guides the coupling member 44 into the pressing tube 42. The exposed portion 60 is moved from the distal end side toward the proximal end side in the extension direction of the opening 52, and is guided to the distal end part of the first opening region 50A.

The exposed portion 60 according to the present embodiment is a pin-shaped projection. When the coupling member 44 reciprocates in the pressing tube 42 in the axial direction, the exposed portion 60 reciprocates in the same way in the opening 50 of the pressing tube 42 (the first opening region 50A, the second opening region 50B, and the third opening region 50C). That is, the exposed portion 60 moves in the opening 50 of the pressing tube 42 in the axial direction of the pressing tube 42 from the proximal end side toward the distal end side in accordance with movement of the coupling member 44 from the proximal end side toward the distal end side, and the exposed portion 60 moves in the opening 50 of the pressing tube 42 in the axial direction of the pressing tube 42 from the distal end side toward the proximal end side in accordance with movement of the coupling member 44 from the distal end side toward the proximal end side. The exposed portion 60 may be called a guide member that prevents rotation and the like of the coupling member 44 when the coupling member 44 reciprocates. The opening region of the first opening region 50A of the opening 50 on the distal end side relative to the middle part, the second opening region 50B, and the third opening region 50C serve as a guide groove for the guide member.

The operation portion of the treatment tool body 14 has an operation portion body, a slider, and the like (not shown).

A distal end part of the operation portion body is attached to a proximal end part of the coil sheath 36.

The slider is a portion that moves the operation wire 40 relative to the coil sheath 36 toward the distal end side or the proximal end side. The slider is slidable relative to the operation portion body toward the distal end side or the proximal end side. A proximal end part of the operation wire 40 is fixed to a distal end part of the slider.

When an operator operates the operation portion of the clip treatment tool 10 and the slider is moved from the distal end side toward the proximal end side relative to the operation portion body, the operation wire 40 is moved from the distal end side toward the proximal end side. When the slider is moved from the proximal end side toward the distal end side relative to the operation portion body, the operation wire 40 is moved from the proximal end side toward the distal end side.

Next, actions of the clip treatment tool 10 will be described.

First, an action that is performed when ligating a treatment part by using the clip unit 12 will be described. In the following description, it is assumed that an insertion portion of an endoscope (not shown) has already been inserted into the body of a patient.

First, when operated by an operator, the insertion portion 34 of the clip treatment tool 10 is inserted from a treatment tool inlet of the endoscope (not shown), and a distal end part of the insertion portion 34 of the clip treatment tool 10, to be more specific, a distal end part of the clip unit 12 is extruded from a treatment tool outlet of the endoscope.

Next, when the operator operates the operation portion of the clip treatment tool 10, the operation wire 40 is moved from the proximal end side toward the distal end side.

In accordance with movement of the operation wire 40 from the proximal end side toward the distal end side, the coupling member 44 and the clip body 16 move from the proximal end side toward the distal end side, and the two arm portions 20A and 20B of the clip body 16 enter an open state as illustrated in FIGS. 1A, 1B, 2A, and 2B.

Next, when operated by the operator, the insertion portion 34 of the clip treatment tool 10 is moved from the proximal end side toward the distal end side, and the distal end parts of the two arm portions 20A and 20B in the open state are pressed against a treatment part.

Next, in the state in which the distal end parts of the two arm portions 20A and 20B in the open state are pressed against the treatment part, when the operator operates the operation portion of the clip treatment tool 10, the operation wire 40 is moved from the distal end side toward the proximal end side.

In accordance with movement of the operation wire 40 from the distal end side toward the proximal end side, the coupling member 44 moves from the distal end side toward the proximal end side, and the exposed portion 60 of the coupling member 44 moves from the distal end side toward the proximal end side along the opening 50 of the pressing tube 42. Moreover, in accordance with movement of the coupling member 44 from the distal end side toward the proximal end side, the clip body 16 moves from the distal end side toward the proximal end side, the two arm portions 20A and 20B are pressed by an end part of the tightening ring 18 on the distal end side in directions toward each other and elastically deform, and the two arm portions 20A and 20B gradually close from the open state.

In a state before the clip body 16 is locked to the tightening ring 18, the two arm portions 20A and 20B open in accordance with movement of the coupling member 44 from the proximal end side toward the distal end side, that is, in accordance with movement of the exposed portion 60 in the first opening region 50A of the pressing tube 42 from the proximal end side toward the distal end side; and the two arm portions 20A and 20B can close in accordance with movement of the coupling member 44 from the distal end side toward the proximal end side, that is, in accordance with movement of the exposed portion 60 in the first opening region 50A of the pressing tube 42 from the distal end side toward the proximal end side.

In accordance with movement of the coupling member 44 from the distal end side toward the proximal end side, that is, in accordance with movement of the exposed portion 60 in the first opening region 50A of the pressing tube 42 from the distal end side toward the proximal end side, the clip body 16 moves from the distal end side toward the proximal end side, the two arm portions 20A and 20B are pressed by the end part of the tightening ring 18 on the distal end side in directions toward each other and elastically deform, and the two arm portions 20A and 20B gradually close from the open state (fully open state) and finally enter a closed state (fully closed state).

On the other hand, in accordance with movement of the coupling member 44 from the proximal end side toward the distal end side, that is, in accordance with movement of the exposed portion 60 in the first opening region 50A from the proximal end side toward the distal end side, the clip body 16 moves from the proximal end side toward the distal end side, and the two arm portions 20A and 20B gradually open from the closed state due to an elastic force and finally enter the open state.

When the clip body 16 moves toward the distal end side or the proximal end side, both end parts of the two arm portions 20A and 20B in the width direction and the inner peripheral surface of the distal end part of the tightening ring body 30 make point contact, and the two arm portions 20A and 20B slide along the inner peripheral surface of the distal end part of the tightening ring body 30.

When the two arm portions 20A and 20B slide along the inner peripheral surface of the distal end part of the tightening ring body 30, the inclined parts of the first protruding portion 24A and the second protruding portion 24B of the two arm portions 20A and 20B and the inclined part of the inner peripheral surface of the distal end part of the tightening ring body 30 function to reduce friction between the two arm portions 20A and 20B and the tightening ring body 30 and to facilitate movement of the clip body 16 relative to the tightening ring 18 toward the distal end side or the proximal end side.

Thus, in the state before the clip body 16 is locked to the tightening ring 18, it is possible to hold a treatment part over again by using the first claw portion 28A and the second claw portion 28B of the two arm portions 20A and 20B by opening and closing the two arm portions 20A and 20B. Therefore, it is possible to hold a target treatment part accurately.

Next, in the state in which the treatment part is held by the first claw portion 28A and the second claw portion 28B of the two arm portions 20A and 20B, the operation wire 40 is moved further from the distal end side toward the proximal end side.

Accordingly, the coupling member 44 and the clip body 16 move further from the distal end side toward the proximal end side. As illustrated in FIGS. 5A, 5B, 6A, and 6B, when the exposed portion 60 moves to a boundary between the first opening region 50A and the second opening region 50B, the tightening ring 18 and the two arm portions 20A and 20B are latched to each other and the two arm portions 20A and 20B enter the closed state.

Figure 5A:
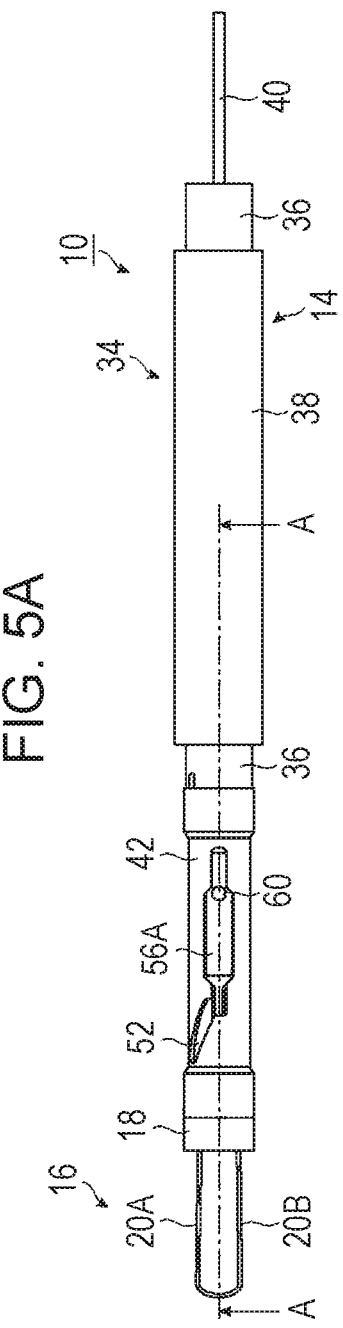
FIG. 5A is a partial external side view of the clip treatment tool according to the embodiment of the present invention, in a state in which the clip body is locked to a tightening ring.
Figure 5B:
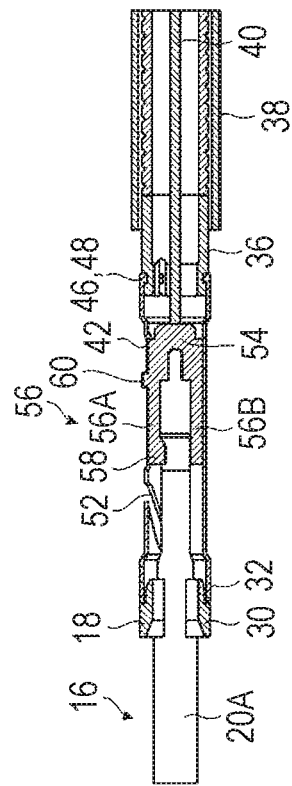
FIG. 5B is a sectional view taken along a chain line A-A in FIG. 5A.
Figure 6A:
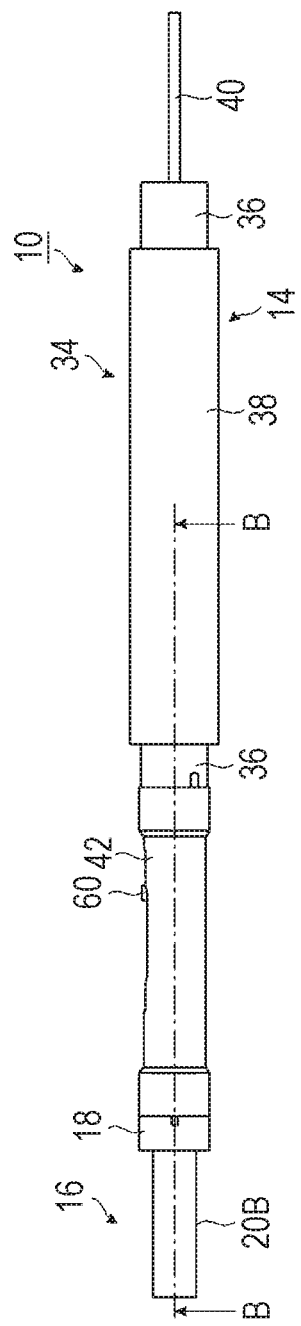
FIG. 6A is a partial external side view of the clip treatment tool according to the embodiment illustrated in FIG. 5A, as seen in a different direction.
Figure 6B:
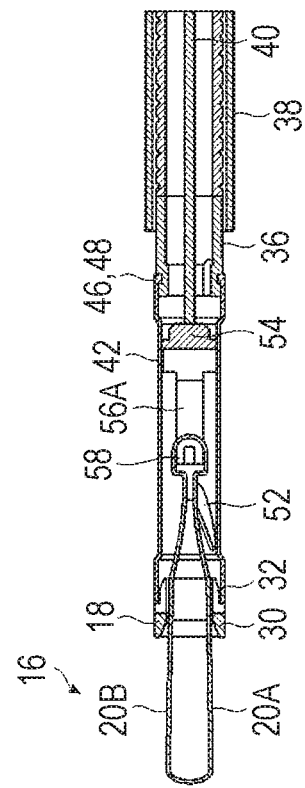
FIG. 6B is a sectional view taken along a chain line B-B in FIG. 6A.
Figure 7A:
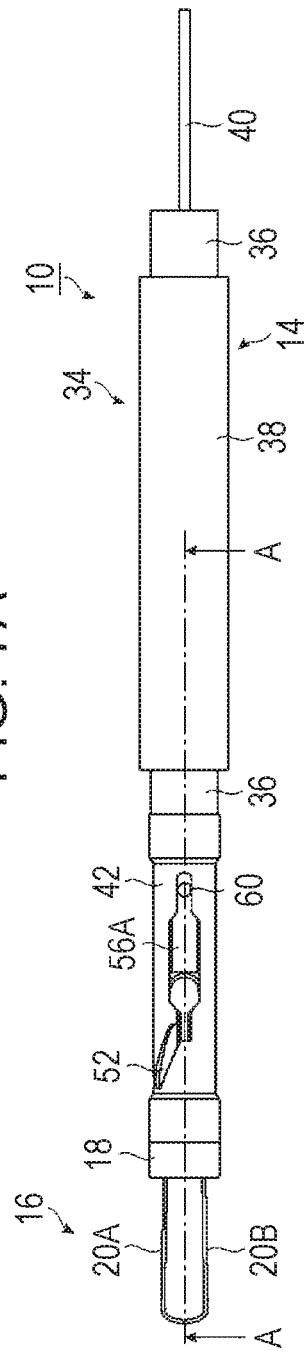
FIG. 7A is a partial external side view of the clip treatment tool according to the embodiment of the present invention, in a state in which a coupling member is separated from the clip body.
Figure 7B:
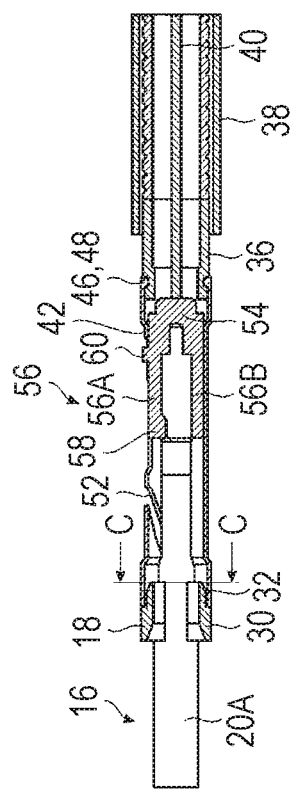
FIG. 7B is a sectional view taken along a chain line A-A in FIG. 7A.
Figure 9A:
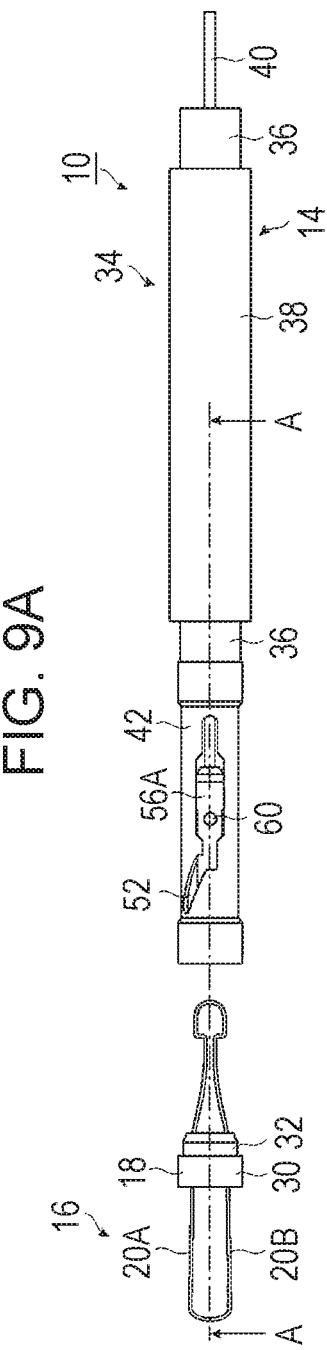
FIG. 9A is a partial external side view of the clip treatment tool according to the embodiment of the present invention, in a state in which a clip unit and the pressing tube are separated from each other.
Figure 9B:
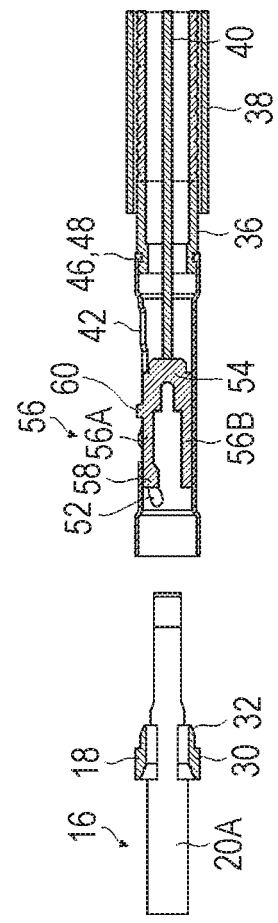
FIG. 9B is a sectional view taken along a chain line A-A in FIG. 9A.
Figure 11:
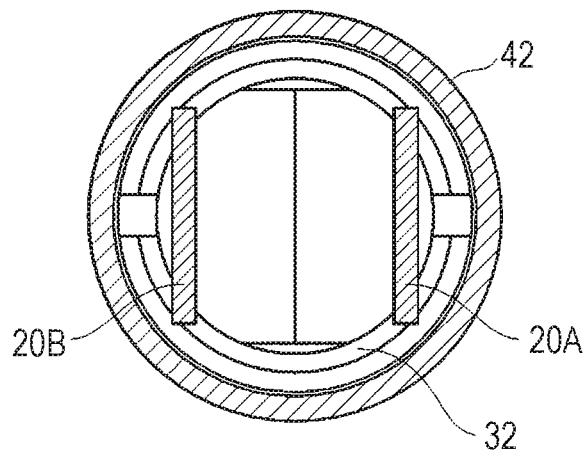
FIG. 11 is a sectional view taken along a chain line C-C in FIG. 7B.

To be more specific, when the coupling member 44 and the clip body 16 move further from the distal end side toward the proximal end side and end parts of the recessed portions of the two arm portions 20A and 20B, that is, the first recessed portion 26A and the second recessed portion 26B on the proximal end side move to positions beyond an end part of the tightening ring 18 on the proximal end side, as illustrated in FIG. 11, the two arm portions 20A and 20B move in directions away from each other (the first direction) due to an elastic force; and, as illustrated in FIG. 5B, the tightening ring 18 is fitted into and latched to the recessed portions 26A and 26B of the two arm portions 20A and 20B, and the two arm portions 20A and 20B enter the closed state.

Thus, as illustrated in FIGS. 5A, 5B, 6A, and 6B, the clip body 16 is locked to the tightening ring 18 while the two arm portions 20A and 20B are in the closed state, and the treatment part is ligated by the first claw portion 28A and the second claw portion 28B of the two arm portions 20A and 20B.

Next, in the state in which the clip body 16 is locked to the tightening ring 18, that is, in the state in which the treatment part is ligated by the first claw portion 28A and the second claw portion 28B of the two arm portions 20A and 20B, the operation wire 40 is moved further from the distal end side toward the proximal end side.

Accordingly, the coupling member 44 and the clip body 16 move further from the distal end side toward the proximal end side, and the exposed portion 60 of the coupling member 44 moves in the second opening region 50B from the distal end side toward the proximal end side.

In accordance with movement of the exposed portion 60 in the second opening region 50B from the distal end side toward the proximal end side, the inclined part of the latch portion 58 of the coupling member 44 moves onto an end part of the folded portion 22 of the clip body 16 on the proximal end side and moves from the distal end side toward the proximal end side, and the distal end part of the first clamping member 56A moves from the middle part of the opening 50 of the pressing tube 42 (the first opening region) toward the outside of the pressing tube 42. That is, the distal end part of the first clamping member 56A is pushed from the middle part of the opening 50 toward the outside of the pressing tube 42.

When the exposed portion 60 moves in the second opening region 50B, because rotation of the exposed portion 60 is restricted by the second opening region 50B that serves as a guide groove, rotation of the coupling member 44 is restricted. Thus, the position of the first clamping member 56A and the position of the opening 50 of the pressing tube 42 are adjusted so as to coincide with each other, and the distal end part of the first clamping member 56A can move from the middle part of the opening 50 of the pressing tube 42 (the first opening region) toward the outside of the pressing tube 42.

The coupling member 44 and the clip body 16 move further from the distal end side toward the proximal end side; and, as illustrated in FIGS. 7A, 7B, 8A, and 8B, the exposed portion 60 moves from the second opening region 50B into the third opening region 50C, the latch portion 58 moves over the end part of the folded portion 22 on the proximal end side, the folded portion 22 and the latch portion 58 are unlatched from each other, and the clip body 16 and the coupling member 44 are separated from each other.

When the coupling member 44 is moved from the distal end side toward the proximal end side in the state in which the folded portion 22 and the latch portion 58 are latched to each other, the inclined surface of the inclined part of the latch portion 58 and an end part of a proximal end part of the folded portion 22 on the first clamping member 56A side make line contact, and the inclined part of the latch portion 58 slides along the end part on the first clamping member 56A side of the proximal end side of the folded portion 22.

When the latch portion 58 slides along the end part of the proximal end part of the folded portion 22 on the first clamping member 56A side, the inclined part of the latch portion 58 functions to reduce friction between the latch portion 58 and the folded portion 22 and to facilitate movement of the latch portion 58 from the distal end side toward the proximal end side relative the folded portion 22.

Next, in the state in which the clip body 16 and the coupling member 44 are separated from each other, the operation wire 40 is moved from the proximal end side toward the distal end side.

In accordance with movement of the operation wire 40 from the proximal end side toward the distal end side, the coupling member 44 moves from the proximal end side toward the distal end side, and the distal end part of the coupling member 44 contacts the proximal end part of the folded portion 22 of the clip body 16. In accordance with further movement of the coupling member 44 from the proximal end side toward the distal end side, the proximal end part of the clip body 16 is pushed by the coupling member 44 toward the distal end side; and, as illustrated in FIGS. 9A, 9B, 10A, and 10B, the tightening ring 18, to which the clip body 16 is locked, and the pressing tube 42 are separated from each other. Thus, in the state in which a treatment part is ligated by the clip unit 12, the clip unit 12 is placed at the treatment part.

Subsequently, when operated by the operator, in the state in which the insertion portion 34 of the clip treatment tool 10 is still inserted into the endoscope, the insertion portion of the endoscope is pulled out from the inside of the body of the patient. To ligate a plurality of treatment parts, the action described above is repeatedly performed.

Next, actions that are performed to remove the clip unit 12 from a treatment part will be described.

First, an action that is performed to remove the clip unit 12 by using a grasping member, such as grasping forceps, will be described.

Figure 12:
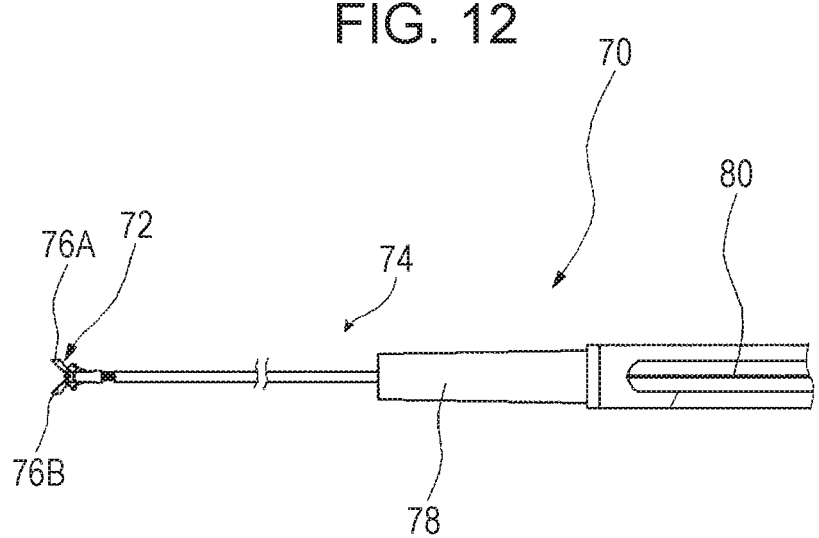
FIG. 12 is a side view illustrating a distal end portion of grasping forceps according to an embodiment.

FIG. 12 is a side view of a distal end portion of grasping forceps according to an embodiment. Grasping forceps 70 illustrated in FIG. 12 include a grasping portion 72, an insertion portion 74, and an operation portion (not shown).

The grasping portion 72 is attached to a distal end part of the insertion portion 74, and the operation portion is attached to a proximal end part of the insertion portion 74.

The grasping portion 72 has a pair of claw members 76A and 76B. The claw members 76A and 76B open and close when an operator operates the operation portion. The claw members 76A and 76B extend from the proximal end side toward the distal end side, and are disposed so as to face each other when grasping surfaces thereof are in a closed state.

The insertion portion 74 includes a sheath 78 and an operation wire 80.

The operation wire 80 is inserted through the inside of the sheath 78 so as to be movable back and forth. The grasping portion 72 is attached to a distal end part of the sheath 78, and a distal end part of the operation wire 80 is fixed to proximal end parts of the claw members 76A and 76B of the grasping portion 72.

When the operator operates the operation portion and the operation wire 80 moves from the distal end side toward the proximal end side, the pair of claw members 76A and 76B enter a closed state (a grasping state). On the other hand, when the operation wire 80 moves from the proximal end side toward the distal end side, the pair of claw members 76A and 76B enter an open state (an ungrasping state).

To remove the clip unit 12, first, when operated by the operator, the insertion portion 74 of the grasping forceps 70 is inserted from a treatment tool inlet of an endoscope (not shown), and the distal end part of the insertion portion 74 of the grasping forceps 70, to be more specific, the grasping portion 72 at the distal end part of the grasping forceps 70 is extruded from a treatment tool outlet of the endoscope.

Next, in the state in which the tightening ring 18 and the pressing tube 42 are separated from each other, that is, in the state in which the clip unit 12 ligates a treatment part and is placed at the treatment part, when the operator operates the operation portion of the grasping forceps 70, the claw members 76A and 76B of the grasping portion 72 of the grasping forceps 70 are caused to enter the open state. Next, the claw members 76A and 76B of the grasping portion 72 in the open state are gradually closed, the tightening ring 18 is pressed by the claw members 76A and 76B of the grasping portion from both sides of the outer peripheral surface in the direction (the first direction) in which the two arm portions 20A and 20B face each other, and the tightening ring 18 is squeezed from the both sides of the outer peripheral surface in the first direction.

Figure 13:
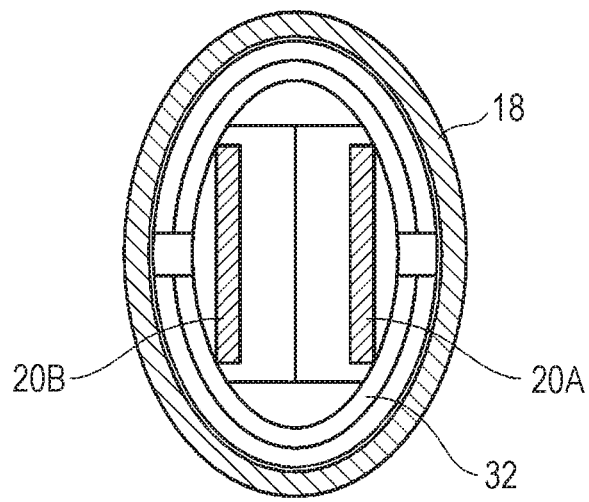
FIG. 13 is a sectional view of an embodiment in a state in which the clip body and the tightening ring are unlocked from a state in which the clip body is locked to the tightening ring as illustrated in FIG. 11.

The tightening ring 18 is squeezed from both sides of the outer peripheral surface in the first direction, and the two arm portions 20A and 20B are moved closer to each other by the inner peripheral surface of the tightening ring 18; and as illustrated in the sectional view of the clip unit 12 in FIG. 13, the ends parts of the recessed portions of the two arm portions 20A and 20B, that is, the end parts of the first recessed portion 26A and the second recessed portion 26B on the proximal end side move to positions where the end parts contact the inner peripheral surface of the tightening ring 18, and the clip body 16 and the tightening ring 18 are unlocked.

Next, in the state in which the clip body 16 and the tightening ring 18 are unlocked, the tightening ring 18 is moved from the distal end side toward the proximal end side relative to the clip body 16. For example, in the state in which the tightening ring 18 is clamped by the claw members 76A and 76B of the grasping portion 72 of the grasping forceps 70, when operated by the operator and in accordance with movement of the grasping forceps 70 move from the distal end side toward the proximal end side, the tightening ring 18 is moved relative to the clip body 16 from the distal end side toward the proximal end side.

In accordance with movement of the tightening ring 18 relative to the clip body 16 from the distal end side toward the proximal end side, the two arm portions 20A and 20B gradually open from the closed state due to an elastic force and finally enter the open state. Thus, the clip unit 12 is removed from the treatment part.

Subsequently, when operated by the operator, in the state in which the insertion portion 74 of the grasping forceps 70 is still inserted into the endoscope, the insertion portion of the endoscope is pulled out from the inside of the body of the patient. For example, in the state in which the tightening ring 18 is clamped by the claw members 76A and 76B of the grasping portion 72 of the grasping forceps 70, the insertion portion of the endoscope is pulled out from the inside of the body of the patient, and the clip unit 12, which has been removed from the treatment part, is also taken to the outside of the body of the patient at the same time. To remove a plurality of clip units 12 from treatment parts, the action described above is repeatedly performed.

Next, an action that is performed to remove the clip unit 12 by using a snare member will be described.

Figure 14:
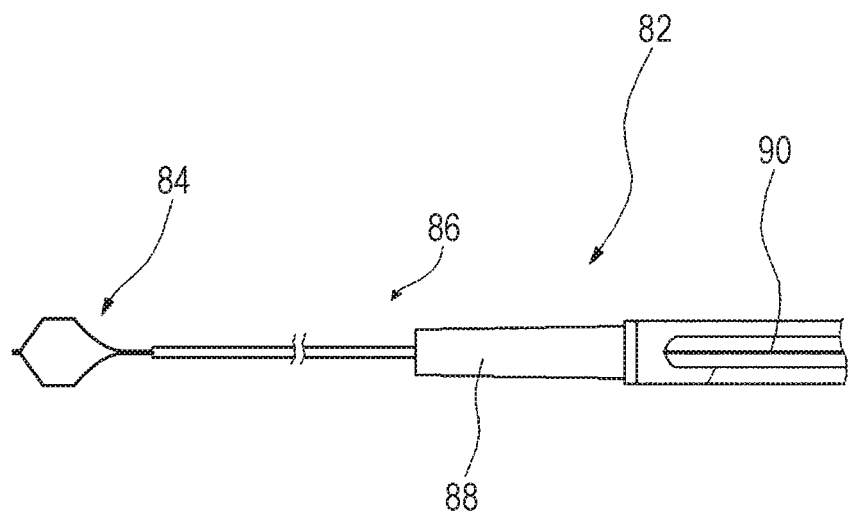
FIG. 14 is a side view illustrating a distal end portion of a snare member according to an embodiment.

FIG. 14 is a side view of a distal end portion of a snare member according to an embodiment. A snare member 82 illustrated in FIG. 14 includes a loop portion 84, an insertion portion 86, and an operation portion (not shown). The loop portion 84 is attached to a distal end part of an operation wire 90 inserted through the inside of the insertion portion 86 described below, and the operation portion is attached to a proximal end part of the insertion portion 86.

The loop portion 84 is formed by bending a wire. The bent portion of the wire is oriented toward the distal end side. When an operator operates the operation portion, the loop diameter of the loop portion 84 decreases.

The insertion portion 86 includes a sheath 88 and the operation wire 90.

The operation wire 90 is inserted through the inside of the sheath so as to be movable back and forth. The loop portion 84 is attached to a distal end part of the sheath 88, and both end parts of the wire of the loop portion 84 are fixed to the distal end part of the operation wire 90.

When the operator operates the operation portion and the operation wire 90 moves from the distal end side toward the proximal end side, the loop portion 84 is inserted into the sheath 88 and the loop diameter of the loop portion 84 decreases. On the other hand, when the operation wire 90 moves from the proximal end side toward the distal end side, the loop portion 84 is extruded from the distal end part of the sheath 88, and the diameter of the loop portion 84 increases.

To remove the clip unit 12, first, when operated by the operator, the insertion portion 86 of the snare member 82 is inserted from a treatment tool inlet of an endoscope (not shown), and the distal end part of the insertion portion 86 of the snare member 82, to be more specific, the loop portion 84 at the distal end part of the snare member 82 is extruded from a treatment tool outlet of the endoscope.

Next, in the state in which the tightening ring 18 and the pressing tube 42 are separated from each other, that is, in the state in which the clip unit 12 ligates a treatment part and is placed at the treatment part, when the operator operates the operation portion of the snare member 82, the loop diameter of the loop portion 84 of the snare member 82 is increased. Next, the loop diameter of the loop portion 84, which has been increased, is gradually reduced, the two arm portions 20A and 20B are fastened by the loop portion 84, and the two arm portions 20A and 20B are pressed from both sides of the outer surface in the direction (the first direction) in which the two arm portions 20A and 20B face each other and are moved in directions toward to each other.

Figure 15:
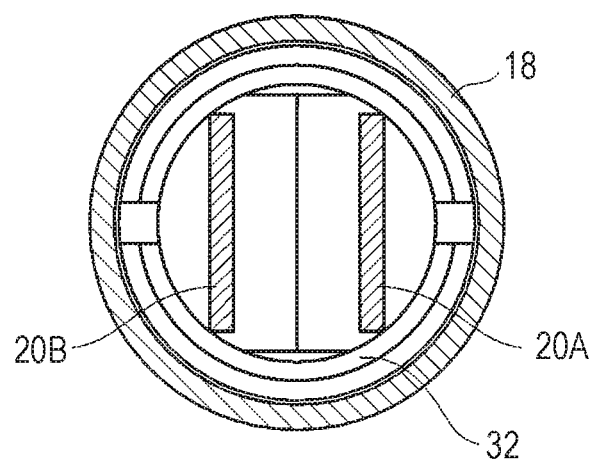
FIG. 15 is a sectional view of an embodiment in a state in which the clip body and the tightening ring are unlocked from a state in which the clip body is locked to the tightening ring as illustrated in FIG. 11.

The two arm portions 20A and 20B are fastened and pressed from both sides of the outer surface in the first direction, and the two arm portions 20A and 20B move closer to each other; and as illustrated in the sectional view of the clip unit 12 in FIG. 15, the end parts of the recessed portions of the two arm portions 20A and 20B, that is, the first recessed portion 26A and the second recessed portion 26B on the proximal end side move to positions where the end parts contact the inner peripheral surface of the tightening ring 18, and the clip body 16 and the tightening ring 18 are unlocked.

Next, in the state in which the clip body 16 and the tightening ring 18 are unlocked, the clip body 16 is moved from the proximal end side toward the distal end side relative to the tightening ring 18. For example, in the state in which the two arm portions 20A and 20B are fastened by the loop portion 84 of the snare member 82, when operated by the operator and in accordance with movement the snare member 82 from the proximal end side toward the distal end side, the clip body 16 is moved from the proximal end side toward the distal end side relative to the tightening ring 18.

In accordance with movement of the clip body 16 relative to the tightening ring 18 from the proximal end side toward the distal end side, the two arm portions 20A and 20B gradually open from the closed state due to an elastic force and finally enter the open state. Thus, the clip unit 12 is removed from the treatment part.

Subsequently, when operated by the operator, in the state in which the insertion portion 86 of the snare member 82 is still inserted into the endoscope, the insertion portion of the endoscope is pulled out from the inside of the body of the patient. For example, in the state in which the two arm portions 20A and 20B are fastened by the loop portion 84 of the snare member 82, the insertion portion of the endoscope is pulled out from the inside of the body of the patient, and the clip unit 12, which has been removed from the treatment part, is also taken to the outside of the body of the patient at the same time. To remove a plurality of clip units 12 from treatment parts, the action described above is repeatedly performed.

With the clip treatment tool 10, until a treatment part is ligated by the clip unit 12, it is possible to hold the treatment part over again by using the two arm portions 20A and 20B, and, after the treatment part has been ligated by the clip unit 12, because the clip body 16 and the tightening ring 18 are locked, it is possible to reliably maintain the state in which the treatment part is ligated by the clip unit 12. Moreover, after the clip unit 12 is placed at the treatment part, it is possible to remove the clip unit 12 from the treatment part by unlocking the clip body 16 and the tightening ring 18 at any desirable timing.

The shapes of the folded portion 22 of the clip body 16 and the latch portion 58 of the coupling member 44 as seen in the second direction are not limited to substantial C-shapes. The shapes are not limited, as long as it is possible to latch the folded portion 22 and the latch portion 58 to each other.

Latching means for latching the clip body 16 and the tightening ring 18 to each other is not limited to fitting of the first recessed portion 26A and the second recessed portion 26B of the two arm portions 20A and 20B into the tightening ring 18. The latching means is not limited, as long as it is possible to latch the clip body 16 and the tightening ring 18 to each other.

The shape and size of the opening 50 of the pressing tube 42 are not limited, as long as at least a part of the exposed portion 60 of the coupling member 44 is exposed from the opening 50 and the distal end side of the first clamping member 56A can move from the opening 50 toward the outside of the pressing tube 42.

Latching means for latching the clip body 16 and the coupling member 44 to each other is not limited to the latch portion 58, as long as it is possible to latch the clip body 16 and the coupling member 44 to each other.

Although the latch portion 58 is provided only on the distal end side of the first clamping member 56A the coupling member 44, a latch portion may be provided also on the distal end side of the second clamping member 56B. In this case, in order that the distal end part of the second clamping member 56B can be pushed toward the outside of the pressing tube 42, an opening, which includes an opening region similar to the middle part of the opening 50, is formed also at a position in the outer surface of the pressing tube 42 facing the outer surface of the second clamping member 56B.

The shape and size of the exposed portion 60 of the coupling member 44 are not limited, as long as at least a part of the exposed portion 60 is exposed from the opening 50 of the pressing tube 42.

Heretofore, the present invention has been described in detail. The present invention is not limited to the embodiment described above, and naturally, various improvements and modifications are possible within the spirit and scope of the present invention.

REFERENCE SIGNS LIST

10 clip treatment tool
12 clip unit
14 treatment tool body
16 clip body
18 tightening ring
20A first arm portion
20B second arm portion
22 folded portion
24A first protruding portion
26A first recessed portion
28A first claw portion
24B second protruding portion
26B second recessed portion
28B second claw portion
30 tightening ring body
32 attachment portion
34, 74, 86 insertion portion
36 coil sheath
38 tube sheath
40, 80, 90 operation wire
42 pressing tube
44 coupling member
46 recessed portion
48 protruding portion
50, 52 opening
50A first opening region
50B second opening region
50C third opening region
54 coupling member body
56 clamping portion
56A first clamping member
56B second clamping member
58 latch portion
60 exposed portion
70 grasping forceps
72 grasping portion
76A, 76B claw member
78, 88 sheath
82 snare member
84 loop portion

What is claimed is:

1. A clip treatment tool comprising:
a clip body that has two arm portions that face each other and open and close and a folded portion that connects proximal end parts of the two arm portions;
a tightening ring that is attached to the two arm portions of the clip body and that functions to close the two arm portions in accordance with a movement of the clip body in a first direction along an axial direction of the clip treatment tool;
a pressing tube that has an opening formed in an outer surface thereof and extending in the axial direction, that has a distal end part to which the tightening ring is removably attached, and that allows the clip body to be contained therein in accordance with the movement of the clip body in the first direction; and
a coupling member that has a distal end part to which the folded portion is removably connected and a proximal end part to which a distal end part of an operation wire is fixed, the coupling member coupling the clip body and the operation wire to each other,
wherein the coupling member is contained in the pressing tube,
wherein, when the clip body moves in the first direction, the clip body is locked to the tightening ring,
wherein, when the clip body is locked to the tightening ring, the tightening ring is configured to be squeezed from both sides of an outer peripheral surface thereof in directions in which the two arm portions face each other, or the two arm portions are configured to be pressed from both sides of outer surfaces thereof in the directions in which the two arm portions face each other, to unlock the clip body and the tightening ring.

2. The clip treatment tool according to claim 1,
wherein the coupling member has an exposed portion at least a part of which is exposed from the opening, the exposed portion moves in the opening in a second direction opposite to the first direction in accordance with a movement of the coupling member in the second direction, and the exposed portion moves in the opening in the first direction in accordance with a movement of the coupling member in the first direction.

3. The clip treatment tool according to claim 2,
wherein the opening has a first opening region, a second opening region, and a third opening region in order from a distal end side of the pressing tube, and
wherein the two arm portions open in accordance with a movement of the exposed portion in the first opening region in the second direction, and the two arm portions close in accordance with a movement of the exposed portion in the first opening region in the first direction.

4. The clip treatment tool according to claim 3,
wherein, in accordance with the movement of the exposed portion in the first opening region in the first direction, the two arm portions are pressed by an end part of the tightening ring on the distal end side in directions toward each other and elastically deform, and the two arm portions gradually close from an open state and enter a closed state; and, in accordance with the movement of the exposed portion in the first opening region in the second direction, the two arm portions gradually open from the closed state due to an elastic force and enter the open state.

5. The clip treatment tool according to claim 4,
wherein, when the exposed portion moves to a boundary between the first opening region and the second opening region, the tightening ring and the two arm portions are latched to each other and the two arm portions enter the closed state, and the clip body is locked to the tightening ring while the two arm portions are in the closed state.

6. The clip treatment tool according to claim 5,
wherein the coupling member has a clamping portion, the clamping portion has a first clamping member and a second clamping member, and the first clamping member has a latch portion on an inner surface of the first clamping member on the distal end side, the inner surface facing the second clamping member,
wherein the folded portion is clamped by the first clamping member and the second clamping member, the folded portion and the latch portion are latched to each other, and the coupling member and the clip body are latched to each other, and
wherein, in a state in which the clip body is locked to the tightening ring, in accordance with a movement of the exposed portion in the second opening region in the first direction, the latch portion moves onto an end part of the folded portion on a proximal end side of the pressing tube and moves in the first direction, a distal end part of the first clamping member moves from the opening toward an outside of the pressing tube, the exposed portion moves from the second opening region into the third opening region, the latch portion moves over the end part of the folded portion on the proximal end side, the folded portion and the latch portion are unlatched from each other, and the clip body and the coupling member are separated from each other.

7. The clip treatment tool according to claim 6,
wherein, in a state in which the clip body and the coupling member are separated from each other, in accordance with a movement of the operation wire in the second direction, the coupling member moves in the second direction, a proximal end part of the clip body is pushed toward the distal end side by the coupling member, and the tightening ring to which the clip body is locked and the pressing tube are separated from each other.

8. An endoscope comprising:
the clip treatment tool according to claim 1; and
a grasping member,
wherein each of the two arm portions has, at both end parts thereof in a width direction, a recessed portion having a length in an extension direction larger than a size of the tightening ring in the axial direction,
wherein, when the clip body moves in the first direction and end parts of the recessed portions on a proximal end side of the pressing tube move to positions beyond an end part of the tightening ring on the proximal end side, the two arm portions move in directions away from each other due to an elastic force, the tightening ring is latched to the recessed portions, and the clip body is locked to the tightening ring,
wherein, in a state in which the tightening ring and the pressing tube are separated from each other, the tightening ring is configured to be squeezed, by the grasping member, from the both sides of the outer peripheral surface thereof in the directions in which the two arm portions face each other, the end parts of the recessed portions on the proximal end side move to positions where the end parts contact an inner peripheral surface of the tightening ring, and the clip body and the tightening ring are unlocked, and
wherein, in a state in which the clip body and the tightening ring are unlocked, in accordance with a movement of the tightening ring, caused by a movement of the grasping member, relative to the clip body in the first direction, the two arm portions open from the closed state and enter the open state.

9. An endoscope comprising:
the clip treatment tool according to claim 1; and
a snare member,
wherein each of the two arm portions has, at both end parts thereof in a width direction, a recessed portion having a length in an extension direction larger than a size of the tightening ring in the axial direction,
wherein, when the clip body moves in the first direction and end parts of the recessed portions on a proximal end side of the pressing tube move to positions beyond an end part of the tightening ring on the proximal end side, the two arm portions move in directions away from each other due to an elastic force, the tightening ring is latched to the recessed portions, and the clip body is locked to the tightening ring,
wherein, in a state in which the tightening ring and the pressing tube are separated from each other, the two arm portions are configured to be pressed, by the snare member, from the both sides of the outer surfaces thereof in the directions in which the two arm portions face each other, the end parts of the recessed portions on the proximal end side move to positions where the end parts contact an inner peripheral surface of the tightening ring, and the clip body and the tightening ring are unlocked, and
wherein, in a state in which the clip body and the tightening ring are unlocked, in accordance with a movement of the clip body, caused by a movement of the snare member, relative to the tightening ring in a second direction opposite to the first direction, the two arm portions open from the closed state and enter the open state.

* * * * *